(12) United States Patent
Harichian et al.

(10) Patent No.: US 7,211,687 B2
(45) Date of Patent: May 1, 2007

(54) PROCESS FOR MAKING CARBOXYALKYLATES OF BRANCHED ALCOHOLS

(75) Inventors: Bijan Harichian, Warren, NJ (US); Jose Guillermo Rosa, Edgewater, NJ (US); Victor De Florio, Cranford, NJ (US)

(73) Assignee: Unilever Home & Personal Care USA, Greenwich, CT (US)

( * ) Notice: Subject to any disclaimer, the term of this patent is extended or adjusted under 35 U.S.C. 154(b) by 252 days.

(21) Appl. No.: 10/926,222

(22) Filed: Aug. 25, 2004

(65) Prior Publication Data

US 2006/0047168 A1   Mar. 2, 2006

(51) Int. Cl.
*C07C 69/02*   (2006.01)
*C07C 59/01*   (2006.01)

(52) U.S. Cl. .................................. 560/187; 562/579

(58) Field of Classification Search ........ 554/151, 554/152, 155, 156, 157; 510/130, 137; 560/187; 562/579
See application file for complete search history.

(56) References Cited

U.S. PATENT DOCUMENTS

| | | | | |
|---|---|---|---|---|
| 1,920,137 | A | 7/1933 | Bruson | 562/588 |
| 5,093,112 | A | 3/1992 | Birtwistle et al. | 424/70 |
| 5,233,087 | A * | 8/1993 | Cripe | 562/537 |
| 5,328,953 | A | 7/1994 | Lynch | 525/332.7 |
| 5,344,850 | A | 9/1994 | Hata et al. | 514/739 |
| 5,756,109 | A | 5/1998 | Burger et al. | 424/401 |
| 6,020,303 | A | 2/2000 | Cripe et al. | 510/503 |
| 6,335,312 | B1 | 1/2002 | Coffindaffer et al. | 510/159 |
| 6,534,073 | B2 | 3/2003 | Harichian et al. | 424/401 |
| 2002/0015717 | A1 * | 2/2002 | Harichian et al. | 424/401 |
| 2004/0013631 | A1 | 1/2004 | Harichian et al. | 424/70.22 |
| 2004/0018948 | A1 | 1/2004 | Harichian et al. | 510/130 |

FOREIGN PATENT DOCUMENTS

| | | |
|---|---|---|
| WO | 99/14180 | 3/1999 |
| WO | 99/18928 | 4/1999 |
| WO | 00/74642 | 12/2000 |

OTHER PUBLICATIONS

Shell Chemicals, 2004, http://www.shellchemicals.com/acetone.*
"Antibacterial and fungicidal activities of heavy metal salts of some beta-alkyloxypropionic Acids" a lecture delivered at the 8th ISF Congress, Budapest, 1966 by Profs. Y. Abe and T. Sakurada, Keio University, Tokyo, Japan.
"Cyanoethylation of alcohols" Medyna, A.P., Volgodon, Filial, NPO "Sintez PAV", USSR, Neftepererab, Neftekhim, (Moscow) (1989)—(with Abstract).
"Alcohol Characteristics" © ExxonMobil, 2000, Rev. 2001.

* cited by examiner

*Primary Examiner*—Rosalynd Keys
(74) *Attorney, Agent, or Firm*—Edward A. Squillante, Jr.; Ellen Plotkin

(57) ABSTRACT

Process for carboxy-alkylation, particularly carboxymethylation, of branched alcohols includes the reaction of isoalcohols with potassium-t-butoxide or sodium-t-butoxide and with salt of halogenated alkanoic acid in the presence of the isoalcohol (starting alcohol) as the solvent. Produced are isoalcohol carboxy-alkylates (preferably, carboxymethylates) in excellent yields and purity.

20 Claims, No Drawings

PROCESS FOR MAKING CARBOXYALKYLATES OF BRANCHED ALCOHOLS

FIELD OF THE INVENTION

The present invention relates to a process for making isoalcohol derivatives. In particular, the present invention relates to a process of making carboxy-alkylates f branched alcohols.

BACKGROUND OF THE INVENTION

Sebum is skin oil which is produced by sebocytes (cells of the sebaceous glands in the skin) and is then secreted to the skin surface. A frequent and undesirable skin condition is "oily skin," the condition which results from the excessive amount of sebum on the skin. Oily skin is associated with a shiny, undesirable appearance and a disagreeable tactile sensation and affects various age groups. Carboxyalkylates of branched alcohols are compounds which provide skin benefits such as sebum suppression.

For example, Harichian et al., U.S. Pat. No. 6,534,073 discloses cosmetic methods and compositions for conditioning human skin by topical application to the skin of cosmetic compositions containing carboxymethylates of branched alcohols. While a process for making carboxymethylates of branched alcohols, and/or ethoxylates thereof is disclosed, a need still exists for even more effective and efficient commercial scale processes, allowing use of smaller amounts and/or less expensive and/or less toxic starting materials, and resulting in overall cost efficiency.

Springman, U.S. Pat. No. 3,992,443 (hereinafter "Springmann '443") discloses a process for the carboxymethylation of alcohols or ether alcohols in a single stage. Springmann '443 teaches the use of both straight chain and branched alcohols as suitable starting alcohols. However, it is believed the carboxymethylation reaction can be run at conditions to further maximize efficiency, ease of industrial scale production, and cost effectiveness.

Harichian et al., Pub. No. U.S. 2004/0018948 and U.S. 2004/0013631 disclose a process of synthesizing a carboxyethylate or higher carboxyalkylate comprising:

(a) combining a branched alcohol with a compound selected from the group consisting of chloroacetic acid, chloropropionic acid, chlorobutyric acid, and mixtures thereof to form a heterogeneous reaction mixture; (b) stirring and heating said heterogeneous reaction mixture at slight reflux under nitrogen;(c) cooling to room temperature; (d) filtering and washing to form a paste; (e) dissolving said paste in water; (f) acidifying with HCl; (g) extracting said acidified paste with chloroform or hexane; (h) removal of chloroform to form the carboxyalkylate compounds.

A need remains for improved processes for making carboxy-alkylates, particularly carboxymethylates, of branched alcohols.

SUMMARY OF THE INVENTION

Shortcomings of the prior art are overcome by the improved process according to the present invention for making compounds of general formula A:

R—O—M    (A)

wherein:
R is a branched alkyl or alkenyl chain having at least 7 carbon atoms, and at least two branches; preferably branched alkyl or alkenyl chain having 13 carbon atoms and at least two branches;

O is an oxygen atom; and
M is (—$(CH_2)_m CO_2 X$); where m is an integer between 1 and 5; and
X is hydrogen, a methyl group, an ethyl group, or a cation. The cation is selected from the group consisting of sodium, lithium, potassium, calcium, copper, magnesium, manganese, strontium, sulfur, zinc, and amines. Preferably, X is hydrogen or a cation.

The first step in the inventive process involves reacting a branched alcohol (ROH) with potassium and/or sodium tertiary butoxide (KTB, K-t-BuO and/or NTB, Na-t-BuO) to form potassium and/or sodium alkoxide (ROK and/or RONa), using the alcohol both as starting material and as reaction solvent. In the alcohol staring material and resulting structures, R is as defined above, preferably R is a branched alkyl or alkenyl chain having 13 carbon atoms and at least two branches. The molar ratio of K-t-BuO/Na-tBuO to Alcohol is about 1:1 to about 1:3, preferably about 1:1.5 to about 1:2. Preferably, the reaction temperature is about 100 deg. C.

In Step II, alkylation, the ROK and/or RONa is reacted with sodium and/or potassium salt of halogenated alkanoic acid. Preferably, sodium salt of chloro-acetic acid (NaClAc or sodium chloroacetate, also referred to as SCA), chloro-propanoic acid, chloro-butanoic acid, chloro-pentanoic acid, or mixtures thereof, is used. The salt (e.g. NaClAc) is in granular of powder form. Preferably, the reaction temperature is about 100 deg. C. This step forms carboxy-alkylate salt (e.g. carboxymethylate, carboxyethylate, carboxypropylate, carboxybutyrate, and/or carboxypentanate sodium salt, respectively).

In Step III, acidification, the alkylated product is reacted with aqueous solution of inorganic acid, such as hydrochloric acid or sulfuric acid (or a mixture thereof), to form carboxyalkyl isoalcohol (e.g. carboxymethyl iso-alcohol).

The carboxy-alkyl (e.g. carboxy-methyl) iso-alcohol may further be reacted with an alcohol or base to form compound of formula A wherein the cation is selected from the group consisting of sodium, lithium, potassium, calcium, copper, magnesium, manganese, strontium, sulfur, zinc, and amines.

In another aspect of the present invention, the process of synthesizing carboxy-alkylates (e.g.) carboxymethylates of branched alcohols includes:

(a) combining a branched alcohol with K-t-BuO/Na-t-BuO to form a KTB/NTB slurry; at least one equivalent of K-t-BuO/Na-t-BuO is needed and alcohol may be used in excess;

(b) adding said KTB/NTB slurry to a slurry of NaClAc (or higher chain acid salt) and branched alcohol over a period of about 2 to about 3 minutes to form a reaction mixture;

(c) stirring said reaction mixture for about 15 to about 20 minutes resulting at a temperature of about 100 deg. C. to about 115 deg. C. at exothermic conditions;

(d) maintaining said reaction temperature at about 100 deg. C. to about 115 deg. C. for about 6 hours;

(e) cooling said reactant mixture after about 6 hours to a temperature of about 60 deg. C. to about 65 deg. C.;

(f) extracting said cooled reaction mixture with acetone to remove excess iso-alcohol and resulting in solidified carboxy-alkylate (e.g. carboxy-Methylate) sodium salt of said alcohol;

(g) acidifying said carboxy-alkylate (e.g. carboxy-Methylate) sodium salt with aqueous solution of HCl;

(h) removing the acetone, water, and volatiles to isolate the compound of formula A.

The reaction steps may be carried out in no particular order, but preferably, the reaction steps are carried out in the particular order of addition described hereinabove in order to maximize yield.

The reaction is carried out in less than about eight hours, preferably about six hours. The reaction is homogenous and product yield is about 80% to about 90%.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the composition, unless otherwise specified.

As used herein, the term "comprising" means including, made up of, composed of, consisting and/or consisting essentially of. Furthermore, in the ordinary meaning of "comprising," the term is defined as not being exhaustive of the steps, components, ingredients, or features to which it refers.

Carboxyalkylates of Branched Alcohols

The inventive process is directed to producing carboxy-alkylate of a branched alcohol of the general formula A (hereinafter "compound A"):

R—O-M   (A)

wherein:
R is a branched alkyl or alkenyl chain having at least 7 carbon atoms, generally from 9 to 15 atoms, and at least two branches;
O is an oxygen atom; and
M is ($-(CH_2)_mCO_2X$), where m is an integer between 1 and 5; and
X is hydrogen, a methyl group, an ethyl group, or a cation. The cation may be selected from the group consisting of sodium, lithium, potassium, calcium, magnesium, manganese, sulfur, and amines including quarternary alkyl amines and polyhydroxy amines, but is not limited thereto.
Preferably, X is a hydrogen or a cation and M is:

—$CH_2CO_2X$   (m is 1).

Accordingly, preferred compounds of formula A are carboxy-methylates of branched alcohols. The most preferred compounds of formula A are carboxy-methyl tridecylisoalcohols (TDCM) and salts thereof.

The branched alkyl chain of the present invention is derived from a branched alcohol having 7 to 15 carbon atoms, preferably at least two branches, as noted above. The preferred alcohols from which the inventive compositions are derived contain a total of at least 9 carbon atoms in order to obtain maximum efficacy, with 13 carbon atoms most preferred. The preferred alcohols from which the inventive compositions are derived, contain from 2 to 5 branches, more preferably 3 to 4 branches, in order to maximize efficacy at minimum cost. The branches may be methyl branches, ethyl branches, or propyl branches. Preferably, the branches are methyl branches or ethyl branches, most preferably methyl branches, due to reduced odor and enhanced efficacy. The alcohol may contain a mix of various chain lengths' alcohols. Such mixed alcohol is suitable in deriving the inventive compositions, as long as the predominant alcohol (at least about 70%) in the mix contains a total of at least 7, preferably at least 9, optimally 13, carbon atoms and at least two branches.

Process for Carboxy-Alkylation of Branched Alcohols

Carboxy-alkylates (e.g. Carboxy-Methylates) of branched alcohols may be synthesized by the following process according to the present invention. Generally, carboxy-alkylation (e.g. carboxy-methylation) of branched alcohol involves the addition of a carboxy-alkyl (e.g. carboxy-methyl )group to the branched alcohol.

Compound of formula A, is derived from branched alcohols which are commercially available, e.g. from Exxon or Henkel.

The following is an illustration of a reaction scheme of the inventive process, advantageously using $C_{13}$ alcohol as both a starting material and as a solvent for the reaction. The numbers in parenthesis below represent molecular weight in grams per mole.

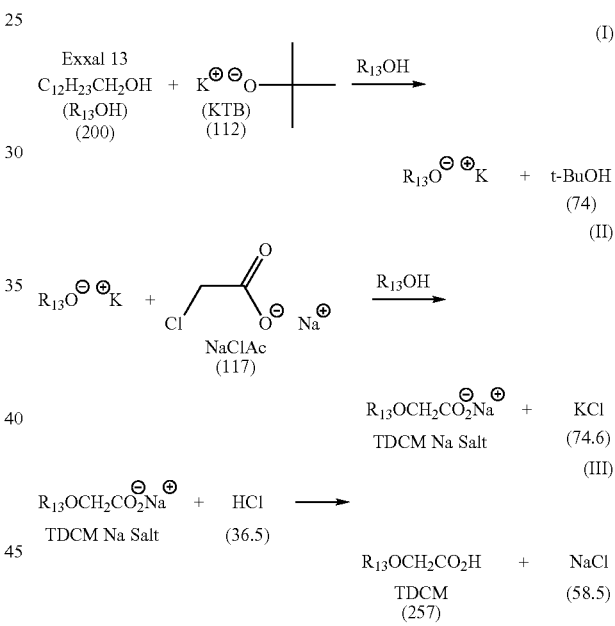

In Step I, a branched alcohol (ROH; R as defined above, i.e., $C_7$+) is reacted with Potassium tertiary-butoxide (KTB or K-t-BuO, available from Sigma-Aldrich Fine Chemicals, Milwaukee, Wis.) to form ROK (potassium alkoxide) in a homogenous solution. The branched alcohol is used both as starting material and as reaction solvent. The K-t-BuO may be used in a 1:1 molar ratio to the branched alcohol, i.e. at least one equivalent of K-t-BuO is preferred. Na-t-BuO may also be used in place of or in combination with K-t-BuO. Preferably, an excess of branched alcohol is used in order to serve as both starting material and reaction solvent, as well as to drive the reaction forward and enhance yield. Without wishing to be bound by theory, it is believed that superior yields are achieved by using the alcohol itself as a solvent, without additional solvent to dilute the reaction mixture, because a more concentrated mixture of reactants is formed. In one preferred embodiment, the molar ratio of K-t-BuO/Na-t-BuO to alcohol is 1:1.5 and a molar ratio of as high about 1:2 or about 1:3 may be used. However, too much alcohol will result in more difficult separation of final product.

In Step II, alkylation, the ROK (and/or RONa; R as defined above, i.e., $C_7+$) is then reacted with sodium and/or potassium salt of halogenated alkanoic acids (e.g. bromo-alkanoic acid, chloro-alkanoic acid). Preferably, sodium salt of chloro-acetic acid (NaClAc), chloro-propanoic acid, chloro-butyric acid, chloro-pentanoic acid, or mixtures thereof, is used to form carboxy-alkylate salt (e.g. in case of NaClAc, carboxymethylate sodium salt) and/or mixtures thereof. The sodium and/or potassium salt of the $C_2$–$C_5$ acid (e.g. NaClAc and/or KClAc) is preferably in granular or powder form, to minimize material cost and simplify processing. The favorable use of solid form halogenated alkanoic acid salt (e.g. NaClAc) is unexpected in view of the physical state of the reagents. Without wishing to be bound by theory, the sodium and/or potassium salt of the halogenated $C_2$–$C_5$ acid appears to drive the reaction forward, compared with its liquid acid form, because it avoids back-protonation of the potassium/sodium alkoxide and/or because it avoids neutralization with K-t-BuO/Na-t-BuO.

This is followed by Step III, acidification of the alkylated product with aqueous solution of acid, such as hydrochloric acid or sulfuric acid, to form carboxy-alkyl (e.g. carboxymethyl) iso-alcohol.

The Steps I, II, and III may be carried out sequentially, simultaneously or in parallel according to the inventive process. Preferably, the steps are carried out in sequential order for maximum efficiency.

The reaction time is relatively quick, preferably, less than about eight hours, more preferably about 6 hours, with minimal addition of heat, as the reaction is substantially exothermic. Temperature control of the reaction is relatively easy, to maintain the reaction temperature at about 50 deg. C. to about 150 deg. C., preferably about 100 deg. C. to about 115 deg. C. Product precipitates/separates out relatively easily, preferably with application of vacuum to remove volatiles. Also, minimal by-products are produced. Product yield is about 80% to about 90%, with typical yield at about 83% for kilogram (commercial scale) process and about 90% for gram (laboratory scale) process. Product purity is about 98% to upwards of about 99%.

The carboxy-methyl isoalcohol may be further reacted with an alcohol or base, such as MeOH or NaOH, to form an R—O-M structure (A) as discussed above, such as wherein X is a methyl group or the cation sodium. While any of the cations as X is generally defined may be used, preferably, sodium salt is used because of commercial availability.

Tridecylcarboxy-Methylate, TDCM, is the most preferred carboxyalkylate of branched alcohol compound, due to water solubility and oil solubility properties which translate into effective skin activity and further to cost effectiveness due to the ability to use a smaller amount of active to gain a given degree of benefit.

Use of the Carboxyalkylate Compounds and Compositions

The compounds and compositions made according to the invention are intended primarily as a product for topical application to human skin, especially as an agent for controlling or preventing excessive sebum secretion. Suppression of sebum provides multiple benefits, including: improved skin condition; reduction of an unpleasant appearance and feel of greasy skin; reduction and/or prevention of acne, rosacea, seborrhea, oily scalp, oily/greasy hair, and dandruff.

In use, a quantity of a composition containing compound A (e.g. TDCM) and a cosmetically acceptable vehicle, for example from 1 to 100 ml, is applied to exposed areas of the skin, from a suitable container or applicator and, if necessary, it is then spread over and/or rubbed into the skin using the hand or fingers or a suitable device.

The composition may also be included in capsules such as those described in U.S. Pat. No. 5,063,057, incorporated by reference herein.

The following specific examples further illustrate the invention, but the invention is not limited thereto.

The branched alcohols listed in the Table below, some of which were used in the Examples, were obtained from Exxon:

TABLE 1

| Trade Name | Branching |
| --- | --- |
| Exxal ® 7 | Mixture of branched and straight chain isomers, about 40% dimethyl pentanols. |
| Exxal ® 8 | Methyl branching only, at least about 38% dimethyl hexanols. |
| Exxal ® 9 | About 33% dimethyl heptanol |
| Exxal ® 10 | Trimethyl heptanols and dimethyl octanols |
| Exxal ® 11 | About 36% dimethyl nonanol |
| Exxal ® 12 | Trimethyl nonanols |
| Exxal ® 13 | Tetramethyl nonanols and trimethyl decanols |
| Nonanol ® | About 80% 3,5,5-trimethylhexanol |
| Acropol 35 ® | About 70% $C_{13}$; about 63% dimethyl branching |

Exxal ® 13 and Acropol 35 ® are preferred alcohols, and Exxal ® 13 is the more preferred alcohol.

EXAMPLE 1

This example provides a procedure for producing TDCM according to the inventive process, on a kilogram scale.

A solution/slurry at 100° C. of 15.5 g-moles of K-t-BuO 95% (Potassium tertiary-butoxide) and 31.0 g-moles of Exxal® 13 alcohol (Branched alcohol with 13 carbons) was added to a slurry at 50–60° C. of 15.5 g-moles of NaClAc 98% and 6.2 g-moles of Exxal® 13 alcohol over a period of 2–3 minutes, resulting in an exotherm from 100 to 115° C. over a 15–20 minute period. Note, the alcohol was being used as a solvent as well as a reactant. Note, also, at least one equivalent of K-t-BuOH is needed for the reaction to occur and/or for the process to be more feasible. The reaction temperature was maintained at 100 to 115° C. over a 6 hour period while the reaction slurry was sampled hourly to monitor the conversion of ROH to TDCM by GC analysis. About 10% w/w of the KTB did not go into solution and remained behind in the makeup vessel. Subsequent treatment of the KTB heel with water and titration of the liberated KOH indicated the presence of 1.45 g-moles.

During the reaction period, the physical character of the slurry changed from yellow with coarse, white solids to an off-white emulsion.

GC analysis indicated that after 1 hour, conversion was 53%, and after 2 hours, 66%. Continued heating beyond the 2 hours resulted in a conversion near 80% as the rate began to level off. After 6 hours of heating, the reaction was cooled to 60–65° C. and diluted with acetone to form a well dispersed slurry.

The slurry was extracted in a 30 gallon Pfaudler vessel with several large volumes of acetone to completely remove excess Exxal. The NaTDCM solidified during these extractions to form a white, waxy, soap-like product and was easily isolated by vacuum-filtration on a large Buchner filter.

In Step III, acidification, the isolated NaTDCM (7+Kg), damp with acetone, was slurried in water overnight during which the pH fell from 10.2 to 9.1, and treated with 20%

HCl to pH 3.0. The upper organic layer was washed repeatedly with brine to remove the bulk of the acetone and TBA, stripped of water and other low boilers at reduced pressure (to 70° C.) and, finally, vacuum-filtered to remove insolubles (NaCl/KCl). Isolated yield=2750 grams.

An additional 250 grams of material was later isolated by working up a composite of heels remaining from the numerous transfers involved in the processing operations. The total isolated yield of 3000 grams represents an 83.1% yield based on the 14.05 g-moles of KTB that actually formed alkoxide.

The amounts of reagents and conditions of the reaction are summarized in the Tables below.

TABLE 1

Charge-in

| Materials | Weight | |
|---|---|---|
| Exxal 13 (brand) iso-alcohol | 7440 g | 37.2 g-moles |
| K-t-Butoxide 95% | 1831 g | 15.5 g-moles |
| NaClAc 98% (granules, available from Akzo-Nobel) | 1851 g | 15.5 g-moles |
| Acetone | 178 Kg | 59 Gallons |
| HCl 20% w/w Aq | 2312 g | ~12.7 g-moles |
| Brine | 13.3 Kg | 3 Gallons |

Exotherm: 100 to 115° C.
Reaction Time: 6 hrs

TABLE 2

Percent Conversion Based on GC Data

| Rxn Time (hrs) | KTB Consumption Assume 100% (%) | KTB Consumption Assume 90% (%) |
|---|---|---|
| 0 | 0 | 0 |
| 1 | 49.6 | 52.7 |
| 2 | 60.8 | 66.4 |
| 3 | 67.0 | 73.2 |
| 4 | 71.9 | 78.5 |
| 5 | 67.0 | 73.2 |

• Yield based on isolated TDCM & consumed KTB: 83.1%

TABLE 3

Acetone Extraction (XTS)

| Acetone | Volume | Exxal13 in TDCM sample |
|---|---|---|
| (1) 54.5 Kg | 18.2 gal | Visible in GC; did not integrate |
| (2) 48.2 Kg | 16.1 gal | Trace |
| (3) 48.2 Kg | 16.1 gal | Trace |
| (4) 27.3 Kg | 9.1 gal | None |

• Isolated Yield of NaTDCM wet with Acetone: 7337 g
• Water Added: 11 Kg; pH 10.2 to 9.1 overnight (not in solution)
• 20% HCl Added: 2312 g~12.7 g-moles

TABLE 4

Brine Washes (4 × 3.3 Kg)

| Wash | Acetone in TDCM (GC Area %) | TBA in TDCM (GC Area %) |
|---|---|---|
| 1 | NA | NA |
| 2 | 8.8 | 0.4 |
| 3 | 4.8 | 0.3 |
| 4 | 3.7 | 0.3 |

• Weight of Crude TDCM after Brine Washing: 3333 g

TABLE 5

Vacuum-strip of Crude at 10–200 mm Hg (Total Time = 3.5 hrs)

| Time of Strip (hrs) | Reaction Temp (° C.) | KF (% $H_2O$) |
|---|---|---|
| 0.5 | 43 to 56 | 3.28 |
| 1.5 | 57 to 73 | 0.59 |
| 3.5 | 70 | 0.12 |

• Vacuum-filtered hot to remove precipitated salts (KCl/NaCl) to yield 2750 g of TDCM Various heels remaining from numerous transfers were combined and worked up, as above, using proportionate amounts of materials to yield another 250 grams of material, assaying by GC>99% (purity).

EXAMPLE 2

The procedure of Example 1 was repeated on laboratory scale, using the same stoichiometric ratios of reagents, but with NaClAc powder, available from Aldrich Chemicals.

Potassium t-butoxide (tBuOK, Aldrich 95%; 3.03 g; 25.7 mmol) was added to a dry 3-neck round bottom flask (50 ml) under a nitrogen atmosphere, followed by EXXAL-13 (Exxon, 10.74 g; 53.7 mmol) and the mixture was heated to 100 deg C. until complete dissolution. At this temperature, the homogeneous solution was transferred to a dry 3-neck round bottom flask (100 ml) containing sodium choloracetate (SCA; Aldrich 98%; 3.05 g; 25.7 mmol) with the aid of additional EXXAL-13 (2.0 g) and the mixture stirred and heated at 100 deg C. for 2 hours. At this time, GC showed 81% conversion to TDCM. The mixture was slowly poured into acetone while stirring vigorously to form white pasty solid. The acetone was decanted and the solid washed with additional acetone, filtered and dried to give a while somewhat sticky solid (7.98 g). The crude material was vigorously stirred in Et2O:3M HCl (100 ml: 50 ml), the layers separated and the Et2O layer washed with saturated NaCl (1×50 ml), dried (Na2SO4; 30 g) and the solvent removed under reduced pressure to give TDCM as a colorless oil (5.2 g; 79%).

The rate of reaction after transfer of the hot alkoxide solution to the NaClAc slurry was much slower in Example 1 than in the smaller-scale lab reaction of this Example, in which the % conversion after 1–2 hours was generally about 80% to about 90+%. One possibility for this slower rate is that the larger particle size of commercial NaClAc, supplied by Akzo-Nobel as granules, may require more time to go into solution than the powder, supplied by Aldrich Chemicals and used for the small lab runs.

EXAMPLE 3

This is a comparative example, showing the importance of using the inventive process as specified, for the synthesis of tridecylcarboxymethylate (TDCM).

Methods and Materials

Gas chromatography (GC) was performed using a Hewlett-Packard 5890 Series II Plus gas chromatograph with an HP 7673 injector controlled by Hewlett-Packard ChemiStation software. The Hewlett-Packard HP-1 column used was 25 M×0.22 mm with a 0.33 um coating of cross-linked methyl silicone. The parameters were as follows:

Inj. temp.=250° C., det. temp.=250° C., initial oven temp.=70° C., initial time=2 min., rate=25° C./min., final oven temp.=250° C. and final time=11 min. Samples were derivatized with Sil-Prep to ensure no unreacted starting material was present.

All solvents were reagent grade and were used as received. All reagents were purchased from the Aldrich or Sigma Chemical Companies and were used as received unless otherwise noted.

Procedures

Using NaOH as the Base 1.0 equivalents of Exxal 13 were charged into a three necked round bottomed flask, followed by 2.1 equivalents of pulverized sodium hydroxide, 16 equivalents of isopropanol and 11 equivalents of water. The flask was equipped with a mechanical stirrer, addition funnel and condenser. The contents were heated at reflux for approximately three hours before being cooled to room temperature.

To the addition funnel were charged 1.0 equivalents of chloroacetic acid. The chloroacetic acid was added dropwise to the flask contents while stirring. Upon completion of the addition, the reaction mixture was stirred at reflux overnight.

After cooling, most of the isopropanol/water solvent was removed under vacuum and the resulting product was dissolved in ether. The ether solution was extracted with 1N HCl, followed by isolation of the organic layer, drying over magnesium sulfate, filtration and concentration under vacuum. Analysis by GC (TMS) indicates little to no TDCM formation.

Using NaOMe as the Base

Another reaction was run using sodium methoxide (with sodium chloroacetate in methanol) as the base with no TDCM product produced.

The comparative example shows that no TDCM is produced when a process different from the inventive one is followed.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention. Throughout this application, various publications have been cited. The entireties of each of these publications are hereby incorporated by reference herein.

What is claimed is:

1. A process of synthesizing a compound of the formula A:

wherein:
R is a branched alkyl or alkenyl chain having at least 7 carbon atoms, and at least two branches;
O is an oxygen atom;
M is ($—(CH_2)_mCO_2X$), where m is an integer between 1 and 5; and
X is hydrogen, a methyl group, an ethyl group, or a cation; comprising:

(a) combining a branched alcohol (ROH), wherein R is as defined above, with potassium and/or sodium t-butoxide to form potassium and/or sodium alkoxide;
wherein said branched alcohol serves as solvent and as reactant;

(b) alkylating said potassium and/or sodium alkoxide with sodium and/or potassium salt of halogenated alkanoic acid to form carboxy-alkylate salt, the solvent consisting essentially of branched alcohol.

2. The process of claim 1, further comprising reacting said carboxy-alkylate salt with aqueous solution of inorganic acid to form carboxy-alkyl iso-alcohol.

3. The process of claim 1, wherein said halogenated alkanoic acid is selected from the group consisting of chloroacetic acid, chloropropanoic acid, chlorobutyric acid, chloropentanoic acid, and mixtures thereof.

4. The process of claim 2, further comprising reacting said carboxy-alkyl iso-alcohol with an alcohol or base to form compound A wherein the cation is selected from the group consisting of sodium, lithium, potassium, calcium, copper, magnesium, manganese, strontium, sulfur, zinc, and amines.

5. The process of claim 1, wherein X is hydrogen or a cation.

6. The process of claim 1, wherein R is a branched alkyl or alkenyl chain having 13 carbon atoms and at least two branches.

7. The process of claim 1, wherein m is 1.

8. The process of claim 1, wherein said salt is NaClAc.

9. The process of claim 1, wherein the reaction steps are carried out in no particular order.

10. The process of claim 1, wherein the reaction steps are carried out in the particular order listed in claim 1.

11. The process of claim 2, wherein said inorganic acid is selected from the group consisting of hydrochloric acid, sulfuric acid, and mixtures thereof.

12. The process of claim 1, wherein said sodium and/or potassium salt of halogenated alkanoic acid is in granular or powder form.

13. The process of claim 1, wherein said process is carried out in less than about eight hours.

14. The process of claim 1, wherein said process results in product yield of about 80% to about 90%.

15. The process of claim 1, wherein said product purity is at least about 98%.

16. The process of claim 1, wherein said process temperature is about 100 deg. C.

17. A process of synthesizing carboxymethylates of branched alcohols comprising:

(a) combining a branched alcohol with K-t-BuO and/or Na-t-BuO to form a KTB and/or NTB slurry, respectively, or mixtures thereof;

(b) adding said KTB and/or NTB slurry to a slurry of NaClAc and branched alcohol over a period of about 2 to about 3 minutes to form a reaction mixture;

(c) stirring said reaction mixture for about 15 to about 20 minutes resulting at a temperature of about 100 deg. C. to about 115 deg. C. at exothermic conditions;

(d) maintaining said reaction temperature at about 100 deg. C. to about 115 deg. C. for about 6 hours;

(e) cooling said reactant mixture after about 6 hours to a temperature of about 60 deg. C. to about 65 deg. C.;

(f) extracting said cooled reaction mixture with acetone to remove excess iso-alcohol to form solidified carboxy-Methylate sodium salt of said alcohol;

(g) acidifying said carboxy-Methylate sodium salt with aqueous solution of HCl;

(h) removing said acetone, water, and volatiles to isolate said compound of formula A.

18. The process of claim 17, wherein said reaction is homogeneous.

19. The process of claim 17, wherein said branched alcohol is used in excess relative to said other reagents.

20. The process of claim 17, wherein the molar ratio of said K-t-BuO to said alcohol is about 1:1 to about 1:3.

* * * * *